US006358944B1

(12) United States Patent
Lederman et al.

(10) Patent No.: US 6,358,944 B1
(45) Date of Patent: Mar. 19, 2002

(54) METHODS AND COMPOSITIONS FOR TREATING GENERALIZED ANXIETY DISORDER

(75) Inventors: Seth Lederman, New York, NY (US); Iredell W. Iglehart, III, Baltimore, MD (US)

(73) Assignee: Vela Pharmaceuticals, Inc., Lawrenceville, NJ (US)

( * ) Notice: Subject to any disclaimer, the term of this patent is extended or adjusted under 35 U.S.C. 154(b) by 12 days.

(21) Appl. No.: 09/638,058

(22) Filed: Aug. 11, 2000

Related U.S. Application Data

(60) Provisional application No. 60/148,881, filed on Aug. 13, 1999, and provisional application No. 60/211,922, filed on Jun. 16, 2000.

(51) Int. Cl.$^7$ ............................................. A01N 43/62
(52) U.S. Cl. ...................... 514/220; 514/271; 514/315; 514/322; 514/336; 514/343; 514/646; 514/647; 514/648; 514/649; 514/650; 514/651; 514/652; 514/653; 514/654; 514/655; 514/656; 424/451; 424/464
(58) Field of Search ................................ 514/220, 271, 514/646, 647, 648, 649, 650, 651, 652, 653, 654, 655, 656, 322, 336, 343, 315; 424/451, 464

(56) References Cited

U.S. PATENT DOCUMENTS 3,882,246 A * 5/1975 Share ........................ 424/330

FOREIGN PATENT DOCUMENTS

| FR | 2100873 | 3/1972 |
| FR | 2121529 | 8/1972 |
| GB | 859187 | 1/1961 |

OTHER PUBLICATIONS

H.R. Khouzam, "Chronic Fatigue Syndrome: Update on Diagnosis and Treatment", *Consultant*, 40(8), pp. 1441–1450 (2000).
C.D. Barnes, et al., "Brainstem noradrenergic system depression by cyclobenzaprine," *Neuropharmacology*, 19, pp. 221–224 (1980).
J.V. Basmajian, "Cyclobenzaprine hydrochloride effect on skeletal muscle spasm in the lumbar region and neck: two double–blind controlled clinical and laboratory studies," *Arch. Phys. Med. Rehabil.*, 59, pp. 58–63 (1978).
R.M. Bennett, et al., "A comparison of cyclobenzaprine and placebo in the management of fibrositis," *Arthritis and Rheumatism*, 31(12), pp. 1535–1542 (1988).
D.G. Borenstein, et al., "Cyclobenzaprine and naproxen versus naproxen alone in the treatment of acute low back pain and muscle spasm," *Clinical Therapeutics*, 12(2), pp. 125–131 (1990).
S, Carette, et al., "Comparison of amitriptyline, cyclobenzaprine, and placebo in the treatment of fibromyalgia," *Arthritis & Rheumatism*, 37(1), pp. 32–40 (1994).

J.W. Commissiong, et al., "Cyclobenzaprine: a possible mechanism of action for its muscle relaxant effect," *Can. J. Physiol. Pharmacol.*, 59, pp. 37–44 (1981).
V. Fossaluzza, et al., "Combined therapy with cyclobenzaprine and ibuprofen in primary fibromyalgia syndrome," *Int. J. Clin. Pharm. Res.*, 12(2), pp. 99–102 (1992).
R.A. Gatter, "Pharmacotherapeutics in fibrositis," *The American Journal of Medicine*, 81(3A), pp. 63–66 (1986).
R.G. Godfrey, "A guide to the understanding and use of tricyclic antidepressants and in the overall management of fibromyalgia and other chronic pain syndromes," *Arch. Intern. Med.*, 156, pp. 1047–1052 (1996).
D.L. Goldenberg, "A review of the role of tricyclic medications in the treatment of fibromyalgia syndrome," *J. Rheumatol.*, 16(19), pp. 137–139 (1989).
D.L. Goldenberg, "Fibromyalgia syndrome a decade later," *Arch. Intern. Med.*, 159, pp. 777–785 (1999).
D.L. Goldenberg, "Treatment of fibromyalgia syndrome," *Rheumatic Disease Clinics of North America*, 15(1), pp. 61–71 (1989).
D. Hamathy, et al, "The plasma endorphin, prostaglandin and catecholamine profile of patients with fibrositis treated with cyclobenzaprine and placebo: a 5–month study," *Journal of Rheumatology*, 16(19), pp. 164–168 (1989).
W.A. Katz, et al., "Cyclobenzaprine in the treatment of acute muscle spasm: review of a decade of clinical experience," *Clinical Therapeutics*, 10(2), pp. 216–228 (1988).
C. Lines, et al., "Lack of sedative and cognitive effects of diphenhydramine and cyclobenzaprine in elderly volunteers," *Journal of Psychopharmacology*, 11(4), pp. 325–329 (1997).
D.R. Miller, et al., "Management of fibromyalgia, a distinct rheumatologic syndrome," *Clinical Pharmacy*, 6, pp. 778–786 (1987).
L.G. Quimby, et al., "A randomized trial of cyclobenzaprine for the treatment of fibromyalgia," *Journal of Rheumatology*, 16(19), pp. 140–143 (1989).
W.J. Reynolds, et al., "The effects of cyclobenzaprine on sleep physiology and symptoms in patients with fibromyalgia," *The Journal of Rheumatology*, 18(3), pp. 452–454 (1991).
T.J. Romano, "Fibromyalgia in children; diagnosis and treatment," *The West Virginia Medical Journal*, 87, pp. 112–114 (1991).
S. Santandrea, et al., "A double–blind crossover study of two cyclobenzaprine regimens in primary fibromyalgia syndrome," *The Journal of International Medical Research*, 21, pp. 74–80 (1993).

(List continued on next page.)

*Primary Examiner*—Frederick Krass
(74) *Attorney, Agent, or Firm*—Fish & Neave; James F. Halsey, Jr.; Elinor K. Shin

(57) ABSTRACT

The present invention relates to methods and compositions comprising a very low dose of cyclobenzaprine or metabolite thereof for preventing and treating Generalized Anxiety Disorder. The present invention further relates to methods and compositions for treating and preventing symptoms associated with Generalized Anxiety Disorder using a very low dose of cyclobenzaprine.

21 Claims, No Drawings

OTHER PUBLICATIONS

N.N. Share, "Cyclobenzaprine: studies on its site of muscle relaxant action in the cat," *Neuropharmacology,* 19, pp. 757–764 (1980).

H.A. Spiller, et al., "Five year multicenter retrospective review of cyclobenzaprine toxicity," *The Journal of Emergency Medicine,* 13(6), pp. 781–785 (1995).

F.J. Villani, et al., "Dialkylaminoalkyl Derivatives of 10,11–Dihydro–5H–dibenzo[a,d]cycloheptene and related compounds," *J. Med. Pharm. Chem.,* 5, pp. 373–383 (1962).

F. Wolfe, et al., "The American College of Rheumatology 1990 criteria for the classification of fibromyalgia," *Arthritis and Rheumatism,* 33(2), pp. 160–172, (1990).

* cited by examiner-

METHODS AND COMPOSITIONS FOR TREATING GENERALIZED ANXIETY DISORDER

This application claims the benefit of U.S. Provisional Application No. 60/148,881, filed Aug. 13, 1999, and claims the benefit of U.S. Provisional Application No. 60/211,922, filed Jun. 16, 2000.

TECHNICAL FIELD OF THE INVENTION

The invention relates to methods and compositions for treating Generalized Anxiety Disorder (GAD) and associated symptoms comprising administering a very low dose of cyclobenzaprine or a metabolite thereof. The invention also relates to compositions comprising a very low dose of cyclobenzaprine or a metabolite thereof.

BACKGROUND OF THE INVENTION

Cyclobenzaprine

Cyclobenzaprine or 3-(5H-Dibenzo[a,d]cyclohepten-5-ylidene)-N,N-dimethyl-1-propanamine, is represented by the chemical formula:

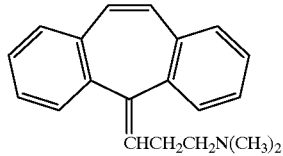

Cyclobenzaprine was first synthesized in 1961. [Villani, F. J., et al., "Dialkylaminoalkyl derivatives of 10,11-dihydro-511-dibenzo a,d cycloheptene and related compounds," *J. Med. Pharm. Chem.* 5:373–383 (1962)]. Cyclobenzaprine was approved by the U.S. Food and Drug Administration in 1977 for the treatment of acute muscle spasms of local origin. [Katz, W., et al., "Cyclobenzaprine in the Treatment of Acute Muscle Spasm: Review of a Decade of Clinical Experience," *Clinical Therapeutics* 10:216–228 (1988)]. Cyclobenzaprine is sold as a hydrochloride salt in a 10 mg non-scored tablet under the tradename Flexeril® (Merck and Co.) or as a generic for use as a skeletal muscle relaxant. The pharmacokinetics of cyclobenzaprine metabolism have been well studied (e.g., Katz, et al., page 219, supra).

No indications of organ toxicity were found in cyclobenzaprine-treated patients at recommended doses. Toxic effects were reported, however, for three individuals who ingested between 260 to 900 mg of cyclobenzaprine. [Katz, et al., "Cyclobenzaprine in the Treatment of Acute Muscle Spasm: Review of a Decade of Clinical Experience," *Clinical Therapeutics* 10:216–228 (1988)]

The principal side effects of cyclobenzaprine treatment are drowsiness, dry mouth or tongue, dizziness and bad taste. [Katz, W. A., et al., supra.] Other less common side effects include nausea, tiredness, constipation, blurred vision, nervousness, confusion, abdominal pain and discomfort.

Generalized Anxiety Disorder

Anxiety disorders are part of a heterogeneous group of psychiatric disorders that are characterized by their predominant symptom being that of anxiety. The Diagnostic and Statistical Manual of Mental Disorders, Fourth Edition (hereinafter, "DSM-IV™") lists twelve different types of Anxiety Disorders. [American Psychiatric Association: Diagnostic and Statistical Manual of Mental Disorders, Fourth Edition. Washingon, D.C., American Psychiatric Association, 1994] These are as follows: Panic Disorder without Agoraphobia; Panic Disorder with Agoraphobia; Agoraphobia without a history of Panic Disorder; Specific Phobia; Social Phobia; Obsessive Compulsive Disorder; Post-traumatic Stress Disorder; Acute Stress Disorder; Generalized Anxiety Disorder; Anxiety Disorder Due to a General Medical Condition; Substance Induced Anxiety Disorder; and Anxiety Disorder not Otherwise Specified.

Generalized Anxiety Disorder (GAD) is the most common anxiety disorder among Americans, though exact incidence and prevalence rates are unknown. People with GAD feel anxious and tense all day long, and their fear is not limited to specific situations. The intensity, duration or frequency of the anxiety and worry is far out of proportion to the actual likelihood or impact of the feared event. The person finds it difficult to keep worrisome thoughts from interfering with attention to tasks at hand and has diffulculty stopping the worry. Adults with GAD often worry about everyday, routine life circumstances (e.g., possible job responsibilities, finances the health of family members, misfortune to their children, or minor matters (such as household chores, car repairs, or being late for appointments).

GAD occurs in both children and adults and was formerly called Overanxious Disorders of Childhood. Children with this disorder tend to worry excessively about their competence or the quality of their work and they may become overly conforming, perfectionist and unsure of themselves. Labellarte, M J, et al, "The Treatment of Anxiety Disorders in Children and Adolescents," Biol. Psychiatry, 46(11): 1567–78 (1999).

Ordinary practitioners in the art (e.g., clinicians and physicians) will often make diagnoses which refer to the GAD as either primary or secondary. These classifications merely indicate whether the most prominent symptoms the patient is experiencing stem from GAD, as is true with a diagnosis of primary GAD, or from another illness or disorder with concomitant symptoms of GAD also emerging, as is the case with secondary GAD. Rogers, M P et al. "Comparing Primary and Secondary Generalized Anxiety Disorder in a long-term Naturalistic Study of Anxiety Disorders," Depress Anxiety, 10(1):1–7, (1999).

A diagnosis of GAD is distinguishable from a diagnosis of non-pathological anxiety, other Anxiety disorders (e.g., Anxiety Disorder due to a General Medical Condition, Substance-Induced Anxiety Disorder) and Axis I disorders based on patient history, laboratory findings and/or physical examination. Patients suffering from GAD meet the criteria set forth in DSM-IV™. Thus, patients suffering from GAD, as opposed to non-pathological anxiety, have worries that are more difficult to control, pervasive, pronounced, distressing, longer in duration and typically interfere significantly with functioning. The worries frequently occur without precipitants and are much less likely to be accompanied by physical symptoms in adults. Generally, if the anxiety or worry solely arises etiologically from a general medical condition (e.g., pheochomocytoma, hyperthyroidism) or taking drugs or if the anxiety is confined to a feature of an Axis I disorder, then GAD is not diagnosed. For example, with regard to Axis I Disorders, patients suffering from excessive worry that is confined to having a Panic Attack (Panic Disorder), being embarrassed in public (Social Phobia), being contaminated (Obsessive-Compulsive Disorder), gaining weight (Anorexia Nervosa), having a serious illness (Hypochondriasis), being away from home or from close relations (Separation Anxiety Disorder) would be diagnosed with the appropriate Axis I disorder.

Various drugs including barbiturates and benzodiapines are often prescribed as primary anxiolytics, while antihistamines, tricyclic antidepressants, antipsychotics and beta-blockers have been prescribed for their secondary anxiolyticiolitic properties. These treatments for Generalized Anxiety Disorder have not proved to be satisfactory due to less than sufficient efficacy, distressing side effects, or addictive qualities.

SUMMARY OF THE INVENTION

The present invention provides methods for treating a human suffering from GAD using a very low dose of cyclobenzaprine, a metabolite thereof, or a pharmaceutically acceptable salt of cyclobenzaprine or metabolite thereof.

The present invention also provides a composition comprising a very low dose of cyclobenzaprine or a metabolite thereof, prepared as a single unit or pre-prepared as a unit separable into portions, each portion of which comprises a very low dose of cyclobenzaprine or metabolite thereof.

The composition is a dosage form of cyclobenzaprine that is useful for treating GAD and is better and effective for treating patients needing treatment with cyclobenzaprine than previous dosage forms of cyclobenzaprine. The composition also allows practitioners to determine and prescribe the appropriate dosage regimen of cyclobenzaprine with a precision and accuracy previously not possible. A composition according to this invention may additionally comprise one or more therapeutic agents such as barbiturates, benzodiazepines, antihistamines, TCAs, SSRIs, atypical antidepressants, antipsychotics and/or beta-blockers.

DETAILED DESCRIPTION OF THE INVENTION

Cyclobenzaprine is a compound having the chemical formula:

Hereinafter, the terms "cyclobenzaprine or metabolite thereof" or "cyclobenzaprine or a metabolite thereof" includes cyclobenzaprine or a metabolite thereof, prodrugs of cyclobenzaprine or a metabolite thereof, or a pharmaceutically acceptable salt, hydrate, or solvate of cyclobenzaprine or a metabolite thereof.

A "very low dose" of cyclobenzaprine or metabolite thereof according to this invention is an amount of cyclobenzaprine or metabolite thereof that is less than 5 mgs.

Metabolites of cyclobenzaprine useful according to the methods of this invention are metabolites that have substantially the same activity or better as cyclobenzaprine in alleviating GAD or one of more of the symptoms of his/her illness. Cyclobenzaprine metabolites that may be useful according to this invention include CBP 10,11-trans-dihydriol, N-desmethyl-2-hydroxycyclobenzaprine, 3-hydroxycyclobenzaprine, N-desmethylcyclobezaprine cyclobenzaprine N-oxide or a chiral isomer of these metabolites.

Pharmaceutical salts of cyclobenzaprine useful according to the methods of this invention are salts prepared from pharmaceutically acceptable non-toxic acids including inorganic acids and organic acids. In one preferred embodiment, the salt is a hydrochloride salt.

A prodrug of cyclobenzaprine is a derivative of cyclobenzaprine that is metabolized in vivo into the active agent. Prodrugs useful according to this invention are those that have substantially the same activity or better than cyclobenzaprine in treating or preventing GAD or one or more of the symptoms of this disorder. Methods for making prodrugs are readily known in the art (e.g., Balant, L. P., "Prodrugs for the Improvement of Drug Absorption Via Different Routes of Administration," *Eur. J. Drug Metab. Pharmacokinet.* 15:143–153 (1990); and Bundgaard, H., "Novel Chemical Approaches in Prodrug Design," *Drugs of the Future* 16:443–458 (1991); incorporated by reference herein).

A composition according the present invention comprises less than 5 mg of cyclobenzaprine, a metabolite thereof or a pharmaceutically acceptable salt of cyclobenzaprine or the metabolite, as a single unit, or as a unit that is pre-prepared into separable portions, each portion of which comprises a very low dose of cyclobenzaprine or the metabolite. In one embodiment, the composition or each portion of the separable composition comprises less than or equal to 2.5 mgs of cyclobenzaprine or the metabolite. In another embodiment, the composition or each portion of the separable composition comprises less than or equal to 1 mg of cyclobenzaprine or the metabolite. For example, a separable composition is a scored tablet.

A composition according the present invention may also comprise one or more other therapeutic agents selected from the group consisting of barbiturates, benzodiazipines, antihistamines, tricyclic antidepressants (TCAs), serotonin reuptake inhibitors (SSRIs), atypical antidepressants, antipsychotics and beta-blockers.

A human to be treated for Generalized Anxiety Disorder (GAD) according to this invention will meet the diagnosis criteria and characteristics described in DSM-IV (1994, supra, incorporated by reference herein). The essential feature of GAD is excessive anxiety or worry (apprehensive expectation), occurring more days than not for a period of at least 6 months, about a plurality of events or activities. The diagnostic criteria for GAD comprises the following:

A. Excessive anxiety and worry, occurring more days than not for at least 6 months, about a plurality of events or activities (such as work or school performance);

B. the patient finds it difficult to control the worry;

C. the anxiety and worry are associated with three (or more) of the following six symptoms (with at least some symptoms present for more days than not for the past 6 months) selected from the group consisting of:
 (1) restlessness or feeling keyed up or on edge;
 (2) being easily fatigued;
 (3) difficulty concentrating or mind going blank;
 (4) irritability;
 (5) muscle tension; and
 (6) sleep disturbance (difficulty falling or staying asleep, or restless unsatisfying sleep).

D. The focus of anxiety is not confined to features of an Axis I disorder (as described in the DSM-IV™);

E. The anxiety, worry, or physical symptoms cause clinically significant distress or impairment in social, occupational, or other important areas of functioning; and F. The disturbance is not due to the direct physiological effects of a substance or a general medical condition and does not occur exclusively during a Mood Disorder, a Psychotic Disorder, or a Pervasive Development Disorder.

The human suffering from GAD according to this invention (i.e., the patient) includes a child. The GAD may be accompanied or exacerbated by another illness or disorder (secondary GAD). In one embodiment of this invention, the GAD in the human to be treated is accerbated by the inability to exercise during waking hours due to injury or other extenuating circumstances, such as lack of time or venues for exercise.

Symptoms of GAD include anxiety (feelings of apprehension, foreboding, or dread) or worry that is difficult to control, general emotional upset as well as nonspecific physical symptoms like shortness of breath, stress, gastrointestinal upset, palpitations, fatigue, muscle aches, tension, sweating, light-headedness, hot or cold flashes, numbness and tingling, feelings of unreality, or insomnia.

In a preferred embodiment, the patient will experience a reduction in anxiety and/or non-specific physical symptoms selected from the group consisting of shortness of breath, stress, gastrointestinal upset, palpitations, fatigue, muscle tension, muscle aches and insomnia.

Barbiturates according to this invention include phenobarbital, amobarbital, probarbital, butabarbital, mephobarbital, pentobarbital, secobarbital, and talbutal.

Benzodiazepines according to this invention according to this invention include chlordiazepoxide, clorazepate, diazepam, flurazepam, halazepam, prazepam, alprazolam, chlonazepam, flunitrazepam, lorazepam, midazolam, oxazepam, quazepam, temazepam, triazolam, estazolam, and troazolam.

Antihistamines according to this invention include diphenhydramine hydrochloride, carbinoxamine maleate, clemastine fumarate, tripelennamine citrate, tripelennamine hydrochloride, pyrilamine maleate, chlorpheniramine maleate, brompheniramine maleate, dexchlorpheniramine maleate, tripolidine hydrochloride, methdilazine, methdilazine hydrochloride, promethazine hydrochloride, trimeprazine tartrate, azatadine maleate, cyproheptadine hydrochloride, diphenylpyraline hydrochloride, hyrdoxyzine hydrochloride, hydroxyzine pamoate, phenindamine tartrate, terfenadine, astemizole, and acrivastine.

TCAs according to this invention may be selected from the group consisting of imipramine, trimipramine, nortriptyline, amitriptyline (Elavil™), doxepin, protriptyline, clomipramine, amoxapine, or desipramine. In a preferred embodiment, the TCA is nefazodone (Serzone™).

SSRIs according to this invention may be selected from the group consisting of fluoxetine (Prozac™), fluvoxamine maleate (Luvox™), paroxetine (Paxil™, Seroxar™, or Aropax™), sertraline (Zoloft™), acelexa, and citalopram (Celexa™). In a preferred embodiment, the SSRI is sertraline (Zoloft™)

Atypical antidepressants are antidepressants which are not TCAs or SSRIs, e.g., serotonin agonist and reuptake inhibitors (SARIs) such as nefazodone (Serzone™) or trazodone (Desyrel™); Norepinephrine-Dopamine Reuptake Inhibitors (NDRIs) such as bupropion (Wellbutrin™); norepinephrine reuptake inhibitors (NRIs) such as reboxetine (Edronax™ or Vestra™) and serotonin-norepinephrine reuptake inhibitors (SNRIs) such as venlafaxine (Effexor™), amoxapine and maprotiline; and tetracyclic atypical antidepressants such as mirtazapine (Remeron™).

Antipsychotics according to this invention are fluphenazine, haloperidol, thiothixene, trifluoperazine, perphenazine, molindone, loxapine, prochlorperazine, acetophenazine, triflupromazine, mesoridazine, chlorpromazine, chlorprothixene, mesoridazine, clozapine, pimozide, risperidone, quetiapine, olanzapine, and thioridazine.

Beta blockers according to this invention are sotalol, timolol, esmolol, cartelol, propranolol, betaxolol, penbutolol, metaprolol, acebutolol, atenolol, and bisoprolol.

Said therapeutic agent according to the methods of this invention may be administered before, during or after the administration of cyclobenzaprine or metabolite thereof.

According to the methods of this invention, very low dose cyclobenzaprine or a metabolite thereof, may be administered sequentially or concurrently with other standard treatments for somatic or psychological illnesses and disorders.

The period of treatment should be carried out for as long as necessary to alleviate one or more of the symptoms of the illness being treated, either in a single, uninterrupted session of visits or in discrete sessions. For example, if a symptom of GAD is being treated, the treatments will preferably be carried out such that the patient achieves alleviation or remission of such symptom. Alternatively, treatments may be carried out until the patient feels generally relieved of all symptoms of GAD. Generally, cyclobenzaprine therapy can be carried out indefinitely to alleviate the symptoms of interest and frequency of dosage may be changed to be taken as needed. In one embodiment, the patient suffering from GAD is treated with less than 5 mgs of cyclobenzaprine or a metabolite thereof/day.

Any suitable route of administration may be employed for providing the patient with an effective dosage of cyclobenzaprine or metabolite thereof. For example, oral, rectal, parenteral, transdermal, subcutaneous, sublingual, intranasal, intramuscular, intrathecal and the like may be employed as appropriate. The term parenteral as used herein includes subcutaneous, intracutaneous, intravenous, intramuscular, intra-articular, intrasynovial, intrasternal, intrathecal, intralesional and intracranial injection or infusion techniques.

Dosage forms include tablets, scored tablets, coated tablets, caplets, capsules (e.g. hard gelatin capsules), troches, dragees, dispersions, suspensions, solutions, patches and the like, including sustained release formulations well known in the art. In one preferred embodiment, the dosage form is a scored tablet.

The compositions and separable compositions useful according to this invention include those suitable for oral, rectal, transdermal, sublingual, and parenteral administration (including subcutaneous, intramuscular, intrathecal and intravenous), although the most suitable route in any given case will depend on the nature and/or severity of the condition being treated. A preferred route of administration according to the methods of the present invention is the oral route. The composition may be conveniently presented in unit dosage form and prepared by any of the methods well-known in the art of pharmacy.

The compositions or separable compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The compositions according to this invention may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

Compositions or separable compositions of this invention may also be administered in the form of suppositories for rectal administration. These compositions or separable compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The composition of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A typical oral formulation for coated tablets would consist of the following:

| Formula | Quantity per Tablet (mg.) |
|---|---|
| cyclobenzaprine | 1.0 |
| Lactose | 74.0 |
| Corn Starch | 35.0 |
| Water (per thousand Tablets) | 30.0 ml* |
| Magnesium Stearate | 1.0 |
| Corn Starch | 25.0 |

*The water evaporates during manufacture.

The active ingredient (cyclobenzaprine) is blended with the lactose until a uniform blend is formed. The smaller quantity of corn starch is blended with a suitable quantity of water to form a corn starch paste. This is then mixed with said uniform blend until a uniform wet mass is formed. The remaining corn starch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration.

Tablets are coated by standard aqueous or nonaqueous techniques. For example, 2.5 mg of hydroxypropylmethylcellulose can be dissolved in 25 mg of deionized water. An aqueous (10 mg) suspension of 1.88 mg talc, 0.5 mg of titanium dioxide, 0.1 mg of yellow iron oxide, and 0.02 mg of red iron oxide is stirred into this solution. The coating suspension is sprayed on the tablets and the coated tablets are dried overnight at 45° C.

Quantification of improvement may be measured according to methods known in the art. For example, standardized instruments such as Zung Anxiety Self Assessment Scale, the Hamilton Anxiety and Depression Scale, the Cori Anxiety Scale, the Irritability-Depression-Anxiety Scale and the Crown-Crisp Experimental Index may be used to measure existence and levels of symptoms. In addition, a clinician or physician may use verbal interviews such as the Hopkins Symptoms Checklist in order to make such assessments. practitioner may reliably assess changes in condition by comparing the treatment results over a time span.

The magnitude of a prophylactic or therapeutic dose of the active ingredient (i.e., cyclobenzaprine or metabolite thereof) in the prevention or treatment of a human will vary with the type of affliction, the severity of the patient's affliction and the route of administration. The dose and dose frequency will also vary according to the age, weight and response of the individual patient. In a preferred embodiment, the dosage will not equal or exceed 5 mgs per day.

The treating physician will know how to increase, decrease or interrupt treatment based upon patient response. Generally, however, treatment or prevention of an illness treated according to the methods of this invention will be timed to coincide with exposure to biochemical or environmental stimuli likely to trigger illness and psychological disorder, and the symptoms thereof, treatable according to this invention or symptoms thereof.

The various terms described above such as "therapeutically effective amount," are encompassed by the above-described dosage amounts and dose frequency schedule.

Throughout this specification and claims, the word "comprise," or variations such as "comprises" or "comprising," will be understood to imply the inclusion of a stated integer or group of integers but not the exclusion of any other integer or group of integers.

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

The contents of the documents cited herein including U.S. application Ser. No. 60/148,881, are hereby incorporated by reference.

We claim:

1. A method for treating or preventing Generalized Anxiety Disorder (GAD) comprising the step of administering to a human in need thereof, a composition comprising cyclobenzaprine or a metabolite thereof in an amount of less than 5 mg/day.

2. A method for treating or preventing symptoms associated with Generalized Anxiety Disorder comprising the step of administering to a human in need of treatment for or prevention of GAD a composition comprising cyclobenzaprine or a metabolite or salt thereof in an amount of less than 5 mg/day.

3. The method according to claim 2 wherein the symptom is selected from the group consisting of anxiety, shortness of breath, stress, gastrointestinal upset, palpitations, fatigue, muscle aches, tension, sweating, light-headedness, hot or cold flashes, numbness and tingling, feelings of unreality and insomnia.

4. The method according to claim 1 or 2, wherein a symptom treated is anxiety.

5. The method according to claim 1 or 2, wherein cyclobenzaprine or the metabolite thereof is administered in an amount of 2.5 mg or less per day.

6. The method according to claim 1 or 2, wherein cyclobenzaprine or the metabolite thereof is administered in an amount of 1.0 mg or less per day.

7. The method according to claim 1 or 2, wherein cyclobenzaprine or the metabolite thereof is administered in combination with psychotherapy.

8. The method according to claim 1 or 2, wherein cyclobenzaprine or the metabolite thereof is administered in combination with a second drug for treatment of another illness or disorder or symptoms thereof.

9. The method according to claim 1 or 2, wherein cyclobenzaprine is administered as a hydrochloride salt.

10. The method according to claim 1 or 2, further comprising the step of administering a second therapeutic agent sequentially or concurrently with cyclobenzaprine or the metabolite thereof.

11. The method according to claim 10, wherein the therapeutic agent is selected from the group consisting of a barbiturate, a benzodiapine, an antihistamine, a tricyclic antidepressant (TCA), a selective serotonin-reuptake inhibitor (SSRI), an atypical antidepressant, an antipsychotic and a beta-blocker.

12. The method according to claim 11, wherein the barbiturate is selected from the group consisting of phenobarbital, amobarbital, probarbital, butabarbital, mephobarbital, pentobarbital, secobarbital and talbutal.

13. The method according to claim 11, wherein the benzodiapine is selected from the group consisting of chlordiazepoxide, clorazepate, diazepam, flurazepam, halazepam, prazepam, alprazolam, chlonazepam, flunitrazepam, lorazepam, midazolam, oxazepam, quazepam, temazepam and troazolam.

14. The method according to claim 11, wherein the antihistamine is selected from the group consisting of diphenhydramine hydrochloride, carbinoxamine maleate, clemastine fumarate, tripelennamine citrate, tripelennamine hydrochloride, pyrilamine maleate, chlorpheniramine maleate, brompheniramine maleate, dexchlorpheniramine maleate, tripolidine hydrochloride, methdilazine, methdilazine hydrochloride, promethazine hydrochloride, trimeprazine tartrate, azatadine maleate, cyproheptadine hydrochloride, diphenylpyraline hydrochloride, hyrdoxyzine hydrochloride, hydroxyzine pamoate, phenindamine tartrate, terfenadine, astemizole, and acrivastine.

15. The method according to claim 11, wherein the TCA is selected from the group consisting of imipramine, trimipramine, nortriptyline, amitriptyline, doxepin, protriptyline, clomipramine, and desipramine.

16. The method according to claim 11, wherein the SSRI is selected from the group consisting of fluoxetine, fluvoxamine maleate, paroxetine, sertraline, and citalopram.

17. The method according to claim 11, wherein the atypical antidepressant is selected from the group consisting of a serotonin agonist and reuptake inhibitor (SARI); a Norepinephrine-Dopamine Reuptake Inhibitor (NDRI); a norepinephrine reuptake inhibitor (NRI); a serotonin-norepinephrine reuptake inhibitor (SNRI); and a tetracyclic atypical antidepressant.

18. The method according to claim 11, wherein the antipsychotic is selected from the group consisting of fluphenazine, haloperidol, thiothixene, trifluoperazine, perphenazine, molindone, loxapine, prochlorperazine, acetophenazine, triflupromazine, mesoridazine, chlorpromazine, chlorprothixene, mesoridazine, clozapine, pimozide, risperidone, quetiapine, olanzapine, and thioridazine.

19. The method according to claim 11, wherein the beta-blocker is selected from the group consisting of sotalol, timolol, esmolol, cartelol, propranolol, betaxolol, penbutolol, metaprolol, acebutolol, atenolol, and bisoprolol.

20. The method according to claim 1 or 2, wherein the cyclobenzaprine or metabolite thereof is administered orally or parentally.

21. The method according to claim 1 or 2, wherein cyclobenzaprine or the metabolite thereof is administered as a tablet or a capsule.

\* \* \* \* \*